United States Patent
Britton, Jr. et al.

(10) Patent No.: US 6,167,748 B1
(45) Date of Patent: Jan. 2, 2001

(54) CAPACITIVELY READOUT MULTI-ELEMENT SENSOR ARRAY WITH COMMON-MODE CANCELLATION

(75) Inventors: Charles L. Britton, Jr., Alcoa; Robert J. Warmack; William L. Bryan, both of Knoxville; Robert L. Jones, Decatur; Patrick Ian Oden; Thomas Thundat, both of Knoxville, all of TN (US)

(73) Assignees: Lockheed Martin Energy Research Corporation, Oak Ridge; University of Tennessee Research Corporation, Knoxville, both of TN (US)

( * ) Notice: Under 35 U.S.C. 154(b), the term of this patent shall be extended for 0 days.

(21) Appl. No.: 09/144,309

(22) Filed: Aug. 31, 1998

(51) Int. Cl.$^7$ .............................. G01B 7/16; G01M 3/04; G01N 19/10; G01N 27/00; G01N 33/543
(52) U.S. Cl. .......................... 73/24.06; 73/24.01; 73/778; 73/61.49; 73/61.75; 435/6; 435/7.1; 436/501; 436/806; 436/151; 422/88; 422/69; 204/403
(58) Field of Search ................................ 73/24.06, 24.01, 73/24.03, 335.04, 19.03, 61.49, 61.75, 61.79, 64.53, 778, 780; 435/6, 291, 288, 4, 39, 7.1; 436/501, 518, 524, 806, 149, 151; 422/88, 83, 98, 68.1, 69, 82.01; 204/403

(56) References Cited

U.S. PATENT DOCUMENTS

| | | | |
|---|---|---|---|
| Re. 35,544 | 7/1997 | Snow | 73/24.01 |
| 3,828,607 | * 8/1974 | Janzen et al. | 73/23 |
| 4,236,893 | 12/1980 | Rice | 23/230 B |
| 4,242,096 | 12/1980 | Oliveira et al. | 23/230 B |
| 4,584,885 | * 4/1986 | Cadwell | 73/862.61 |
| 4,596,697 | 6/1986 | Ballato | 422/98 |
| 4,637,987 | 1/1987 | Minten et al. | 436/151 |

(List continued on next page.)

FOREIGN PATENT DOCUMENTS

WO 94 28372   12/1994   (WO).

OTHER PUBLICATIONS

MEMS Sensors and Wireless Telemetry for Distributed Systems —C. L. Britton et al., presented at the SPIE 5th International Symposium on Smart Materials and Structures, Mar. 2, 1998, San Diego, California.

Microfabrication of Cantilever Styli for the Atomic Force Microscope —T. R. Albrecht, 1990 American Vacuum Society, pp. 3386–3396, v.

(List continued on next page.)

*Primary Examiner*—Hezron Williams
*Assistant Examiner*—J. David Wiggins
(74) *Attorney, Agent, or Firm*—Hardaway/Mann IPGroup; Nexsen Pruet Jacobs & Pollard, LLP

(57) ABSTRACT

An improved multi-element apparatus for detecting the presence of at least one chemical, biological or physical component in a monitored area comprising an array or single set of the following elements: a capacitive transducer having at least one cantilever spring element secured thereto, the cantilever element having an area thereof coated with a chemical having an affinity for the component to be detected; a pick-up plate positioned adjacent to the cantilever element at a distance such that a capacitance between the cantilever element and the pick-up plate changes as the distance between the cantilever element and the pick-up plate varies, the change in capacitance being a measurable variation; a detection means for measuring the measurable variation in the capacitance between the cantilever element and the pick-up plate that forms a measurement channel signal; and at least one feedback cantilever spring element positioned apart from the coated cantilever element, the cantilever element substantially unaffected by the component being monitored and providing a reference channel signal to the detection means that achieves a common mode cancellation between the measurement channel signal and reference channel signal.

22 Claims, 5 Drawing Sheets

U.S. PATENT DOCUMENTS

| | | | |
|---|---|---|---|
| 4,656,871 | 4/1987 | Czarnocki | 73/724 |
| 4,735,906 | 4/1988 | Bastiaans | 436/527 |
| 4,847,193 | 7/1989 | Richards et al. | 435/6 |
| 4,905,701 | 3/1990 | Cornelius | 128/660.01 |
| 4,906,840 | 3/1990 | Zdeblick et al. | 250/306 |
| 4,999,284 | 3/1991 | Ward et al. | 435/4 |
| 5,001,053 | 3/1991 | Takahashi et al. | 435/7.1 |
| 5,130,257 | 7/1992 | Baer et al. | 436/151 |
| 5,135,852 | 8/1992 | Ebersole et al. | 435/39 |
| 5,156,972 | 10/1992 | Issachar | 435/288 |
| 5,179,028 | 1/1993 | Vali et al. | 436/524 |
| 5,221,415 | 6/1993 | Albrecht et al. | 156/629 |
| 5,283,037 | 2/1994 | Baer et al. | 422/82.01 |
| 5,306,644 | 4/1994 | Myerholtz et al. | 436/149 |
| 5,323,636 | 6/1994 | McGowan et al. | 73/24.01 |
| 5,339,675 | 8/1994 | DiLeo et al. | 73/24.04 |
| 5,363,697 | 11/1994 | Nakagawa | 73/105 |
| 5,372,930 | 12/1994 | Colton et al. | 435/6 |
| 5,411,709 | 5/1995 | Furuki et al. | 422/91 |
| 5,445,008 | 8/1995 | Wachter et al. | 73/24.06 |
| 5,445,970 | 8/1995 | Rohr | 436/526 |
| 5,445,971 | 8/1995 | Rohr | 436/526 |
| 5,477,716 | 12/1995 | Snow | 73/24.01 |
| 5,482,678 | 1/1996 | Sittler | 422/90 |
| 5,494,639 | 2/1996 | Grzegorzewski | 422/82.01 |
| 5,501,986 | 3/1996 | Ward et al. | 436/525 |
| 5,552,274 | 9/1996 | Oyama et al. | 435/6 |
| 5,595,908 | 1/1997 | Fawcett et al. | 435/287.2 |
| 5,658,732 | 8/1997 | Ebersole et al. | 435/6 |
| 5,705,399 | 1/1998 | Larue | 436/501 |
| 5,719,324 | 2/1998 | Thundat et al. | 73/24.01 |
| 5,763,283 * | 6/1998 | Cernosek et al. | 436/183 |
| 5,804,709 * | 9/1998 | Bourgoin et al. | 73/105 |
| 5,936,150 * | 8/1999 | Kobrin et al. | 73/24.06 |
| 5,959,957 * | 9/1999 | Ikeda et al. | 369/127 |
| 6,016,686 * | 1/2000 | Thundat | 73/23.2 |

OTHER PUBLICATIONS

Photothermal Spectroscopy with Femtojoule Sensitivity Using a Micromechanical Device —J. R. Barnes, et al., Nature, vol. 372–3 Nov. 1994, pp. 79–81.

A Mechanical Nanosensor in the Gigahertz Range: Where Mechanics Meets Electronics —Surface Science Letters— 1994.

A Nondestructive Method for Determining the Spring Constant of Cantilevers for Scanning Force Microscopy —J. P. Cleveland et al., Science, vol. 64, No. 2, Feb. 1993.

Observation of a Chemical Reaction Using a Micromechanical Sensor —J. K. Gimzewski et al., Chemical Physics Letters, vol. 217, No. 5.6, pp. 589–594.

Measuring Intermolecular Binding Forces with the Atomic–Force Microscope: The Magnetic Jump Method —Hoh et al., Proceedings, Fifty–Second Annual Meeting Microscopy Society of America, Jul. 31–Sep. 5 1994, pp. 1054–1055.

*Journal of the American Chemical Society* —B. G. Rao et al., Jun. 3, 1992, vol. 114, No. 12.

Sensing Discrete Steptavidin–Biotin Interactions with Atomic Force Microscopy—Gil U. Lee, et al., Langmuir, vol. 10, No. 2, 1994.

A Novel Readout Technique for Capacitive Gas Sensors— *Sensors and Actuators*, B1 (1990), pp. 58–61, U. Schoeneberg, B. J. Hosticka, G. Zimmer and G. J. Maclay.

A Capactive Pressure Sensor With Low Impedance Output and Active Suppression of Parasite Effects, *Sensors and Actuators*, A21–A23 (1990), pp. 108–114, B. Puers, E Peeters, A. Van Den Bossche, and W. Sansen.

* cited by examiner

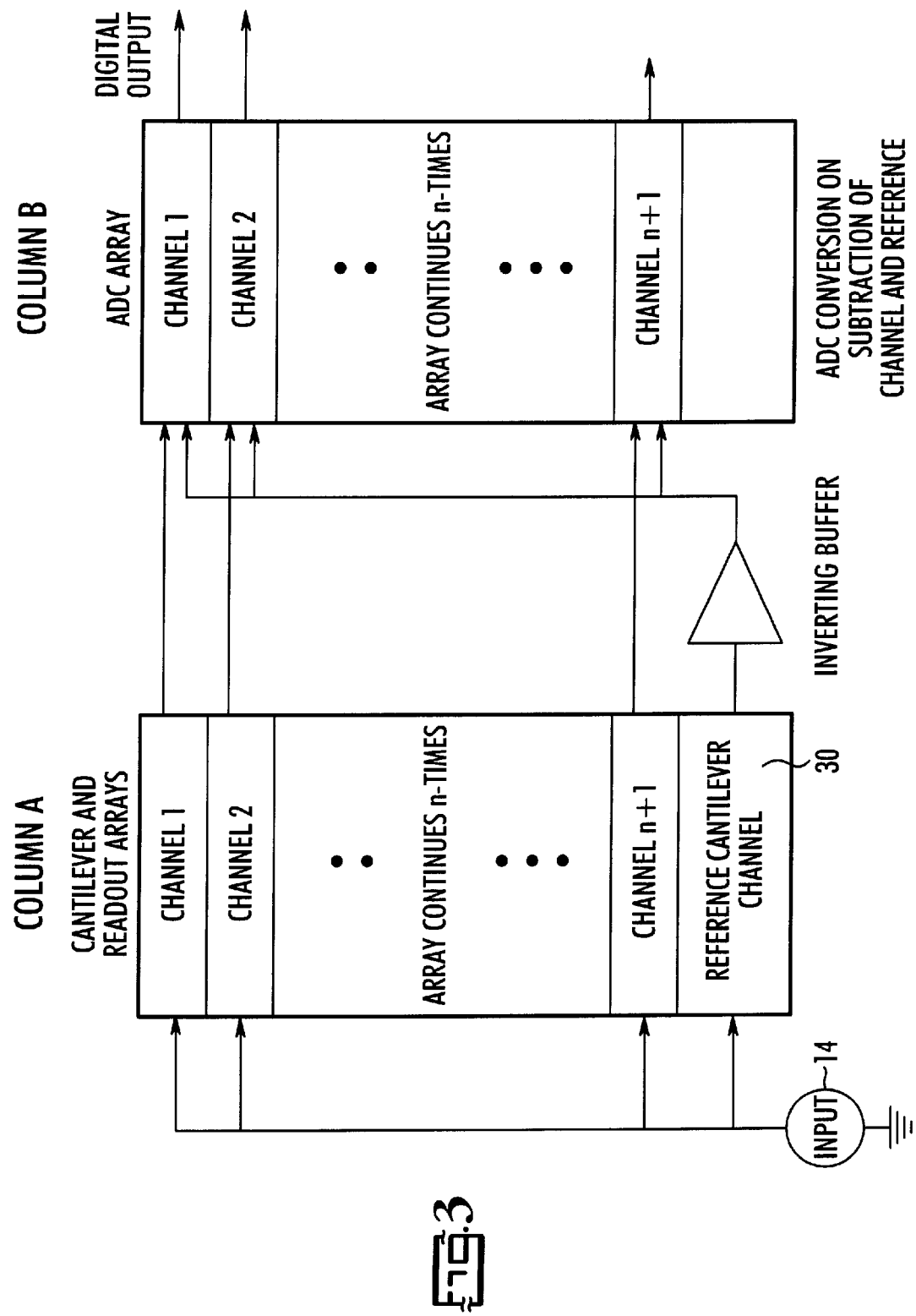

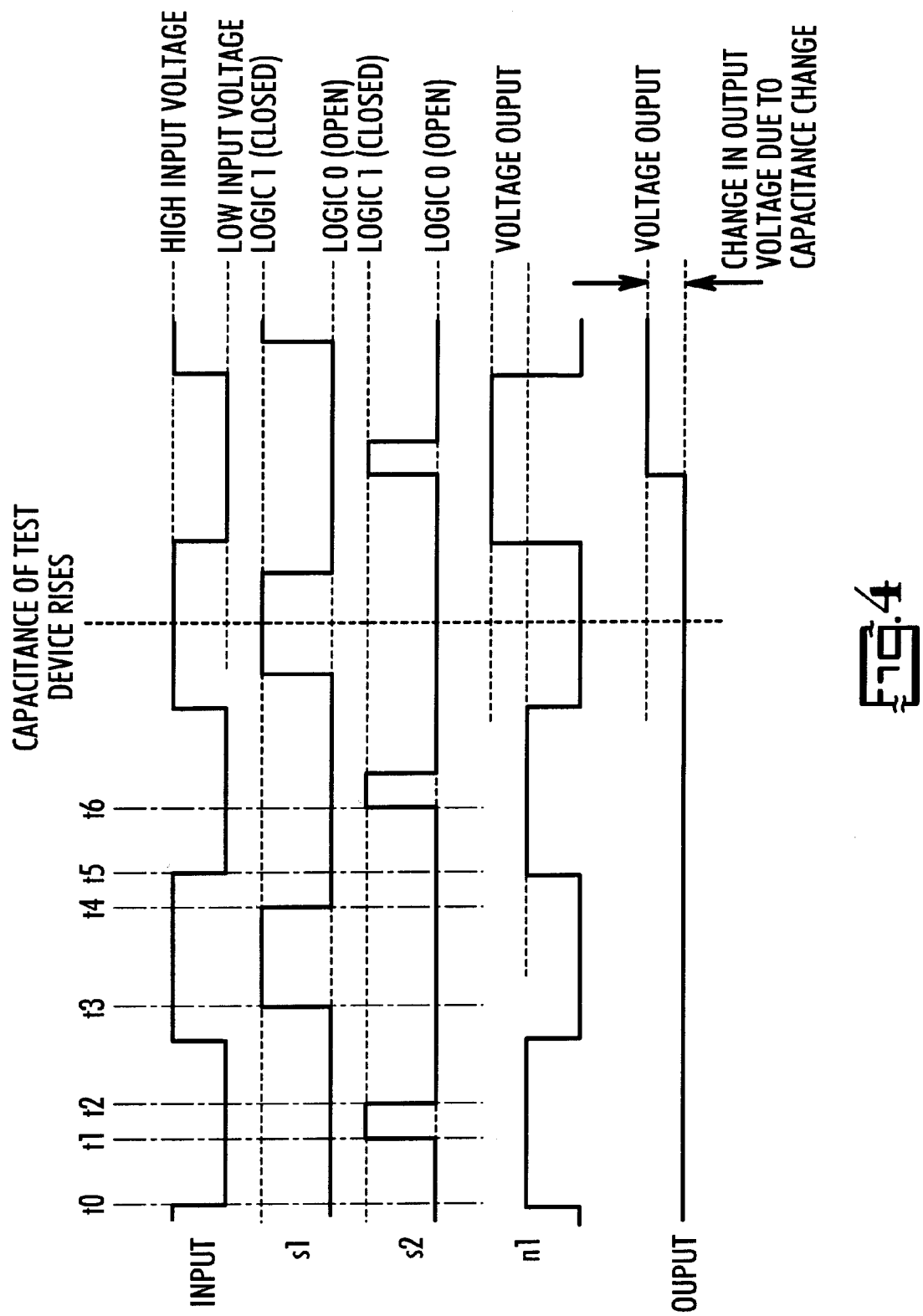

CAPACITIVELY READOUT MULTI-ELEMENT SENSOR ARRAY WITH COMMON-MODE CANCELLATION

This invention was made with Government support under contract DE-AC05-96OR22464 awarded by the U.S. Department of Energy to Lockheed Martin Energy Research Corporation, Inc. and the Government has certain rights in this invention.

FIELD OF THE INVENTION

The present invention relates to instruments for measuring the concentration of a chemical, physical or biological presence or component dispersed within a monitored area. Specifically, the invention relates to a microcantilever sensor which measures the concentration of a chemical, physical or biological presence or component dispersed within a monitored area.

BACKGROUND OF THE INVENTION

A pressing need exists in many industries, disciplines and governmental interests for a highly sensitive and selective detector of quantifying chemical, physical or biological presences or components in a monitored area. To qualify, such a detector must have such diverse characteristics as being small, rugged, inexpensive, selective, reversible and extremely sensitive. Applicants have invented other apparatuses directed to this pressing need in the industry. U.S. Pat. No. 5,719,324 to Thundat and U.S. Pat. No. 5,445,008 to Wachter, incorporated herein by reference and commonly assigned to Applicant, both describe such technology.

These prior art references disclose microcantilever sensor technology which is a next-generation electromechanical technique with broad application in chemical, physical and biological detection. Depending on the dimensions of the microcantilever platform and the cantilever spring constant, deflections of these cantilevers can be detected with sub-Angstrom precision using current techniques employed by atomic force microscopy (AMF) technology such as optical, piezoresistive, piezoelectric, capacitive, and electron tunneling. To date, however, available technology has limited the use of cantilevers to a single read out, normally by optical beams. This use is cumbersome and time consuming.

The present invention focuses on developing arrayable, electronically read cantilevers which are selectively coated with certain chemicals to achieve a sensitivity to a specific physical, chemical or biological presence, e.g., relative humidity, mercury vapor, mercaptan, toluene, viscosity infrared and ultraviolet radiation, flow rate, lead in water, DNA hybridization, and antibody-antigen interaction. The cantilevers of the present invention convert a change in capacitance into a signal which is ultimately converted into a DC voltage output for further processing.

In accordance with the present invention, an array of cantilevers with a variety of different coatings may be placed on a single chip in order to detect the presence of various chemical, physical or biological presences. As the coatings react with the presence or component sensed, the change in stress causes a deflection of the cantilever, thus, changing the space between the cantilever and an associated lower plate. This change is sensed as a change in capacitance.

Sensing electronics associated with the cantilever perform several novel functions. First, the sensing electronics are able to provide a simultaneous or sequential readout of all cantilevers in an array. Second, the sensing electronics utilize a virtual ground on both sides of the cantilever capacitance in order to minimize the effects of stray capacitance, thus, allowing the location of the readout amplifier away from the cantilever without effecting the signal gain. And, third, the sensing electronics utilizes a differential common-mode cancellation to remove from the data the effects of externally caused noises from sources such as power supply variations, preamplifier pickup, or vibration. The same differential operation could also be used to reduce errors caused by temperature, humidity and interfering chemical components.

OBJECTS OF THE INVENTION

It is, thus, an object of the present invention to provide an apparatus and method for measuring concentrations of a chemical, physical or biological presence, that may be present within a monitored area.

It is a further object of the present invention to provide an apparatus for measuring chemical, physical or biological presences, the apparatus being arrayable and electronically read.

It is another object of the present invention to provide an apparatus which is capable of simultaneous read out of arrays.

It is yet a further object of the present invention to provide an apparatus which is capable of providing an output signal reflective of the accumulation of a chemical, physical or biological presence sought to be detected.

It is yet another object of the present invention to provide an apparatus which is capable of providing an output signal free from the effects of stray capacitance and common-mode noises.

BRIEF DESCRIPTION OF THE DRAWINGS

FIG. 3 is a block diagram describing a second embodiment of the present invention.

FIG. 4 is a chart describing the timing utilized in the present invention for controlling the sensing apparatus.

DETAILED DESCRIPTION OF THE PREFERRED EMBODIMENTS OF THE INVENTION

For a better understanding of the present invention, together with other and further objects, advantages and capabilities thereof, reference is made to the following disclosure and appended claims in connection with the above-described drawings.

Figure 1:
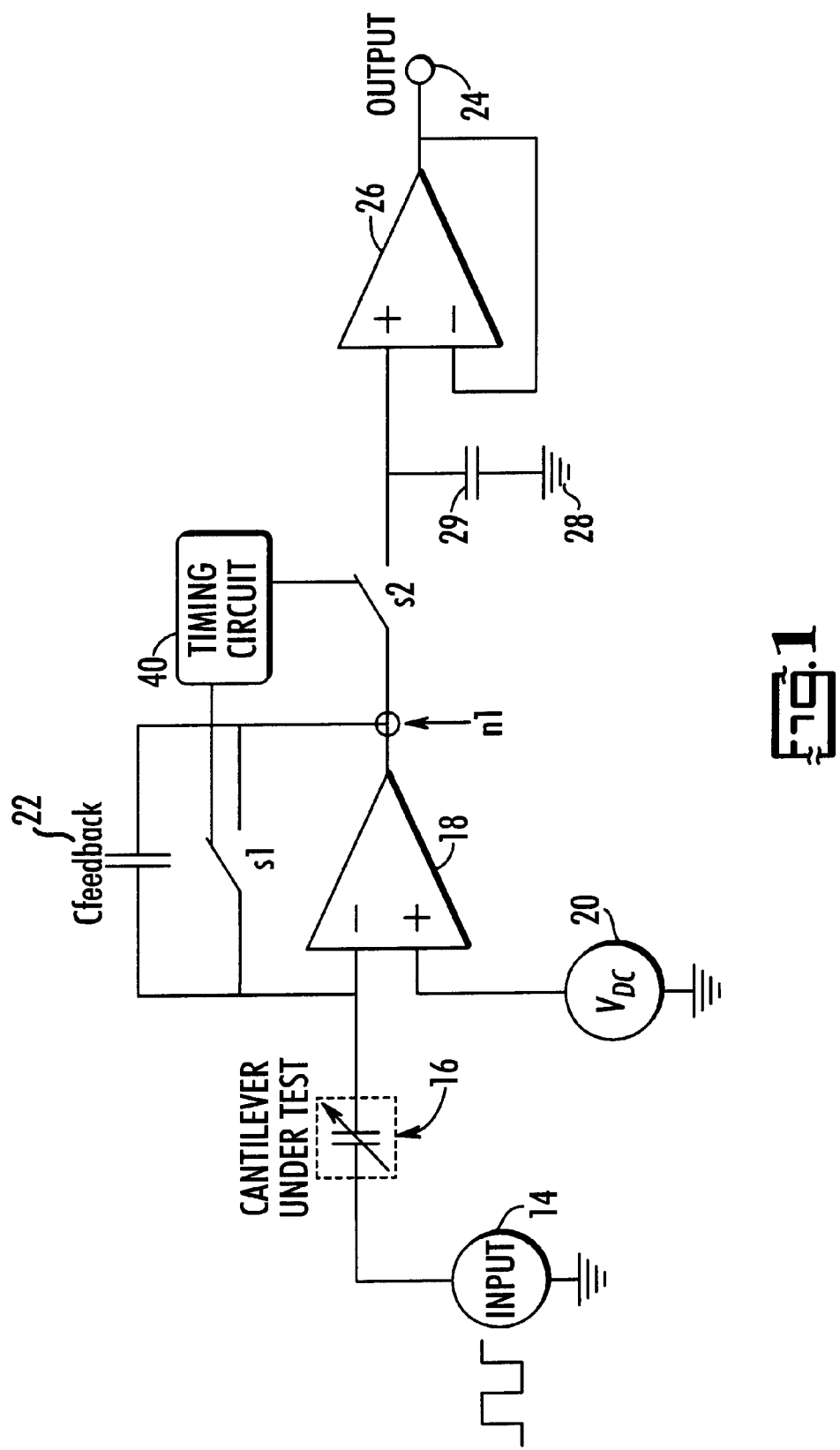
FIG. 1 is a schematic diagram of the electronics of the sensing apparatus.
Figure 1A:
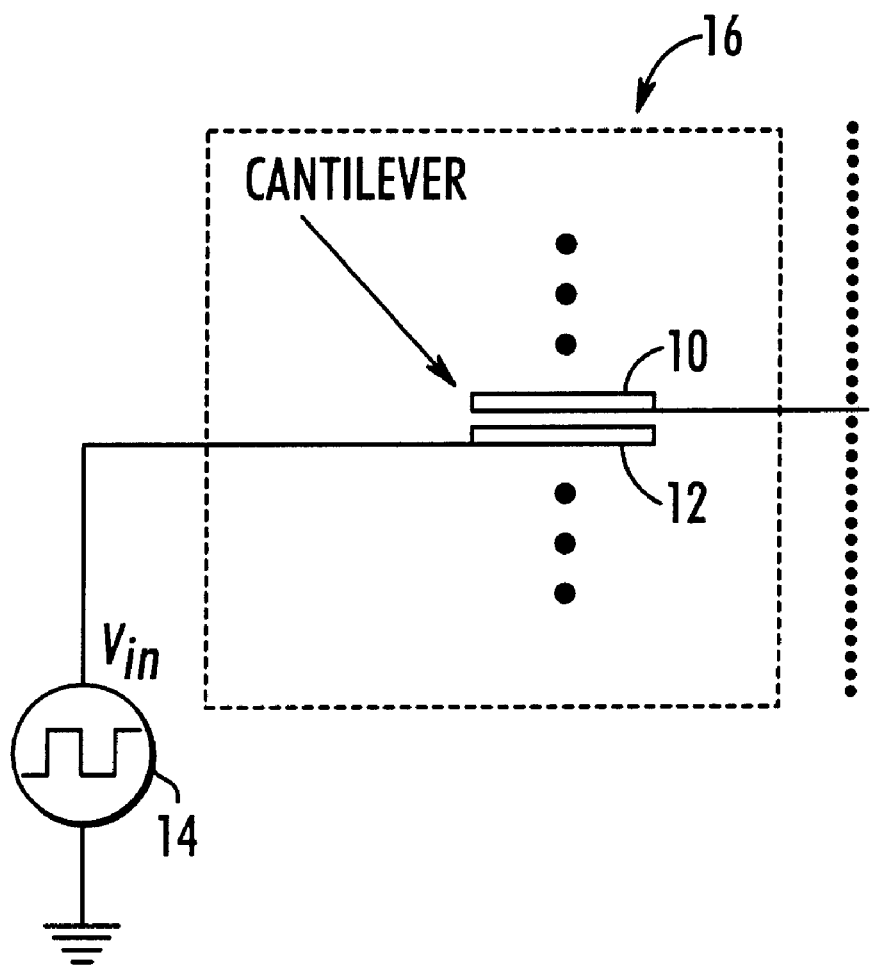
FIG. 1a is an enlarged schematic diagram of the cantilever portion of the sensing apparatus.

FIG. 1 of the drawings discloses a preferred embodiment of the present invention. As seen in FIG. 1 and FIG. 1a, an apparatus 1 for detecting the presence of at least one chemical, biological or physical presence in a monitored area is shown. The apparatus 1 utilizes a cantilever 10 which has an area coated with a chemical having an affinity for the presence or component to be detected. For example, by applying a thin layer of gelatin or other hygroscopic material, humidity can be sensed. By coating silicon-nitride cantilevers with gold on one side, pH changes can be detected. Effects of exposure to ultraviolet radiation can be sensed by choosing the proper polymeric coating, and local radiation dosimetry is even possible by recording radiation-induced changes in cantilever properties.

As the cantilever 10 is exposed to the presence or component for which it has a sensitivity, the coating reacts causing a change in stress and, thus, a deflection in the cantilever 10. As the distance between the cantilever 10 and pick-up plate 12 varies, the capacitance between the cantilever 10 and plate 12 also varies. This change in capacitance is ultimately reflective of the accumulation of the presence or component collected on the coated portion of the cantilever 10. The configuration comprising the cantilever 10 and pick-up plate 12 constitutes a microcantilever sensor 16.

As further shown in FIG. 1, and particularly in FIG. 1a, the pick-up plate 12 of microcantilever sensor 16 is connected to an input source 14 which is a grounded source. In a preferred embodiment, the input source 14 supplies a square wave voltage pulse which drives sensor 16 in the kilohertz frequency range. A signal indicating the capacitance measurable between the cantilever 10 and the pick-up plate 12 is input into a signal modifying device 18. Device 18 is preferably an operational amplifier. In a preferred embodiment, amplifier 18 is in communication with a voltage source 20 which is an independently grounded source. The existence of a grounded input source 14 on one side of cantilever 10 and a virtual ground produced by the feedback action of feedback capacitor 22 and amplifier 18 on the other side of cantilever 10 eliminates the effects of stray capacitance on both ends of the cantilever structure 16. In a preferred embodiment, voltage source 20 is a DC voltage source.

In parallel with the feedback capacitor 22 is a switch S1 which is externally controlled by circuitry, including timing circuit 40. The operation of switch S1 is further described in the discussion of FIG. 4. In general, switch S1 is closed on a high logic signal to reset the feedback capacitor 22 input to amplifier 18. When switch S1 is opened, a signal from the feedback capacitor 22 is restored to the input amplifier 18.

As the signals above described pass through and exit amplifier 18, they pass through a node N1 before being input into the output amplifier 26. Located between node NI and output amplifier 26 is a second switch S2 which is controlled by external circuitry including timing circuit 40. The operation of switch S2 is further described in the discussion of FIG. 4. Switch S2, like switch S1, is closed on a high logic signal and opened on a low logic signal.

The closure of S2 allows for the sampling of the output of amplifier 18. Input capacitor 29 and amplifier 26, grounded at 28, comprise a sample and hold circuit. When S2 is closed, the voltage at N1 is sampled in the circuit. Upon opening switch S2, the circuit retains the voltage of the previous sample until the next sample is taken.

OPERATION OF A FIRST EMBODIMENT OF THE INVENTION

Figure 2:
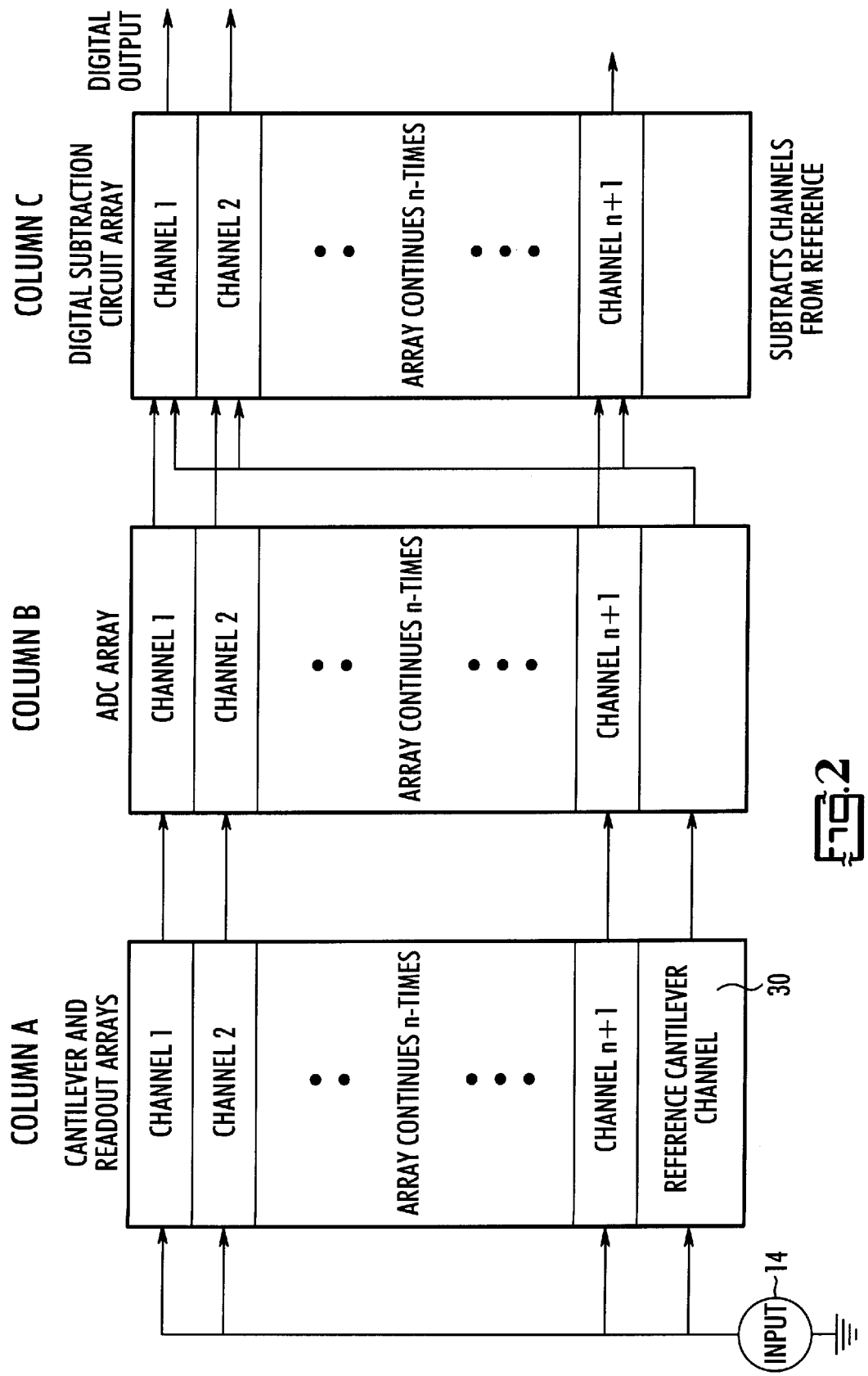
FIG. 2 is a block diagram describing a first embodiment of the present invention.

In further detailing the operation of the apparatus and describing a first embodiment of the invention, we now turn to FIG. 2. As seen in Column A of FIG. 2, the apparatus 1 of FIG. 1 is provided as an array of cantilevers, thus Channel 1 through Channel (n+1) are provided. In a preferred embodiment, a single voltage input 14 may be provided for the array of cantilevers although separate inputs for each cantilever may be utilized without compromising the results of the invention.

At the bottom of Column A, the reference cantilever channel 30 is provided. The signal from reference cantilever channel 30 is made available to the processing elements in column B of FIG. 2. The capacitance produced by the sensor element providing input to channel 30 is produced by an arrangement similar to the arrangement of sensor 16, however, the cantilever associated with reference channel 30 is a non-coated cantilever or a cantilever having a coating unaffected by or minimally affected by the presence or component being detected.

In addition to the output of reference channel 30, the output of apparatus 1 at output 24 is further input into Column B, the output 24 described as follows:

$$V_{out} = V_{dc} + V_{in}(\text{peak-peak})[\Delta C_{in}/C_f]$$

where $V_{in}$(peak–peak) is the peak-to-peak input voltage; $C_{in}$ is the cantilever capacitance 16; $C_f$ is the feedback capacitance 22; $V_{dc}$ is voltage 20; and $V_{out}$ is the output voltage of the apparatus 1.

Column B comprises an analog-to-digital converter (ADC) for further manipulating the channel inputs. In a preferred embodiment, the channel inputs are converted from analog signals to digital signals prior to being further manipulated in the digital subtraction circuit array shown at Column C. At Column C, the digital signals input into each channel are subtracted from the reference cantilever channel 30 input which is provided to each channel. Thus, the digital output for each channel is indicative of a resultant change in capacitance at each channel's respective cantilever in the array. The resultant change in capacitance is ultimately due to an accumulation of the presence or component detected and can be described as follows:

$$\Delta V_{out} = V_{in}(\text{peak-peak})[\Delta C_{in}/C_f]$$

The output of Column C may be further manipulated to determine the quantity of accumulation. In a preferred embodiment, the change in output level is directly proportional to the capacitance exhibited by the monitored cantilever.

OPERATION OF ALTERNATE EMBODIMENT OF THE INVENTION

A second embodiment of the present invention is further detailed in FIG. 3. As seen in FIG. 3, Column A, apparatus 1 is provided as an array of cantilevers, thus Channel 1 through Channel (n+1) are provided. A single voltage input 14 may be provided for the array, although separate inputs may be utilized without affecting the output of apparatus 1.

At the bottom of Column A, the reference cantilever channel 30 is provided. The signal from reference cantilever channel 30 is made available to the processing elements in column B of FIG. 3, the signal first passing through a level shifting buffer positioned between Column A and Column B. The capacitance produced by the sensor element providing input to reference 10. cantilever channel 30 is produced by an arrangement similar to the arrangement of sensor 16. The cantilever associated with reference channel 30, however, is a non-coated cantilever or a cantilever having a coating unaffected by or minimally affected by the presence or component being detected.

Column B, which is adapted to receive inputs from Channel 1 through Channel (n+1), acts as both an analog-to-digital converter (ADC) and a subtraction circuit. In this alternate embodiment, the inputs of Channel 1 through Channel (n+1) are subtracted from the reference cantilever channel 30 input prior to the analog-to-digital conversion. The result of the subtraction, i.e., the resultant signal, is then converted to a digital signal indicative of the resultant change in capacitance at each respective cantilever in the array. As in the first embodiment, the output of the apparatus 1 and the resultant change in capacitance are described by the formulas previously described.

TIMING CIRCUIT OPERATION

A timing circuit 40 is associated with the operation of the present invention to allow for the sampling and resetting at consistent intervals of the output of the apparatus 1. An example showing the operation of the timing circuit 40 associated with the present invention is provided in FIG. 4. As shown in FIG. 4, at an initial period in time t0, input voltage is at its lowest value. At t0, switch S1 and switch S2 (FIG. 1) are in an open position.

At a subsequent time interval t1, switch S2 is closed in order to take a sampling of the output of amplifier 18. Sampling of the output signal from amplifier 18 is taken consistently at specific intervals in the input voltage pattern. As seen in the preferred embodiment, the sample is taken at a point t1 when the input voltage is low and when S1 is in an open position. Sampling is repeated for a time t5 until a change in output voltage is detected.

Between times t2 and t3, the input voltage transitions. At time t3, switch S1 closes, thus, providing a "baseline" value at the output of amplifier 18 equal to the value of voltage ($V_{dc}$) 20. At time t4 switch S1 opens and at time t5 the input transitions in the opposite direction. The output N1 changes in the opposite direction from the input with an amplitude described by the earlier equations. At t6, switch S2 is closed again and samples the output of amplifier 18. The output at node 24 will then be representative of the capacitance of the cantilever.

While there has been shown and described what is at present considered the preferred embodiments of the invention, it will be obvious to those skilled in the art that various changes and modifications can be made therein without departing from the scope of the invention defined by the appended claims.

What is claimed is:

1. An multi-element apparatus for detecting the presence of at least one chemical, physical or biological component in a monitored area comprising the following elements:

a capacitive transducer having at least one cantilever spring element secured thereto, said cantilever element having an area thereof coated with a chemical having an affinity for said component to be detected;

a pick-up plate positioned at a distance away from said cantilever element such that a capacitance between said cantilever element and said pick-up plate changes in response to a change in said distance between said cantilever element and said pick-up plate that forms a measurement channel signal, said change in capacitance being a measurable variation;

a means for detecting said measurable variation in said capacitance between said cantilever element and said pick-up plate; and at least one feedback cantilever spring element substantially unaffected by said component to be detected and positioned apart from the other of said at least one cantilever element, said feedback cantilever element providing a reference channel signal to said detection means for achieving a common mode cancellation between the measurement channel signal and reference channel signal.

2. The apparatus of claim 1 wherein a virtual ground is maintained on both sides of said at least one cantilever element having said coated area, said virtual ground operable to minimize stray capacitance.

3. The apparatus of claim 1 wherein said capacitive transducer produces a first analog signal for input into said detection means, said detection means further comprising an analog-to-digital converter and a subtraction circuit.

4. The apparatus of claim 3, wherein said first analog signal is passed through said analog-to-digital converter to produce a first digital signal related to said capacitance between said cantilever element and said pick-up plate.

5. The apparatus of claim 3 wherein said reference channel signal is a second analog signal, said second analog signal being passed through said analog to digital converter to produce a second digital signal.

6. The apparatus of claim 3 wherein said subtraction circuit subtracts said first digital signal from said second digital signal to produce a resultant signal free from common-mode noises, said resultant signal related to an accumulation of said component on said coated area of said at least one cantilever.

7. The apparatus of claim 6 wherein said first analog signal and said second analog signal are passed through said subtraction circuit to produce said resultant signal prior to said resultant signal passing to said analog-to-digital converter.

8. The apparatus of claim 1 wherein said detection means further comprises a timing circuit, said timing circuit operable to generate said resultant signal.

9. The apparatus of claim 8 wherein said timing circuit is operable to reset said detection means at an interval in time.

10. An multi-element apparatus for detecting the presence of at least one chemical, biological or physical component in a monitored area comprising the following elements:

a capacitive transducer having at least one cantilever spring element secured thereto, said cantilever element having an area thereof coated with a chemical having an affinity for said component to be detected;

a pick-up plate positioned adjacent to said cantilever element at a distance such that a capacitance between said cantilever element and said pick-up plate changes as said distance between said cantilever element and said pick-up plate varies, said change in capacitance being a measurable variation;

an input voltage source electrically connected to said capacitive transducer, said input voltage driving said transducer;

a means for detecting said measurable variation in said capacitance between said cantilever element and said pick-up plate that forms a measurement channel signal; and at least one feedback cantilever spring element positioned apart from the other of said cantilever elements, said feedback cantilever element providing a reference channel signal to said detection means for achieving a common mode cancellation between the measurements channel signal and referring channel signal.

11. The apparatus of claim 10 wherein a virtual ground is maintained on both sides of said at least one cantilever having said coated area, said virtual ground operable to minimize stray capacitance.

12. The apparatus of claim 10 wherein a first analog signal is produced by said a capacitive transducer for input into said detection means, said detection means further comprising an analog-to-digital converter and a subtraction circuit.

13. The apparatus of claim 12, wherein said first analog signal is passed through said analog-to-digital converter to produce a first digital signal equivalent to said capacitance between said cantilever element and said pick-up plate.

14. The apparatus of claim 12 wherein said feedback capacitance signal is a second analog signal, said second analog signal being passed through said analog-to-digital converter to produce a second digital signal equivalent to said reference channel signal.

15. The apparatus of claim 12 wherein said first digital signal is subtracted from said second digital signal by said subtraction circuit to produce a resultant signal free from common-mode noises, said resultant signal related to an accumulation of said component on said coated area of said cantilever element.

16. The apparatus of claim 15 wherein said first analog signal and said second analog signal are passed through said subtraction circuit to produce said resultant signal prior to said resultant signal passing to said analog-to-digital converter.

17. The apparatus of claim 10 wherein said detection means further comprises a timing circuit, said timing circuit operable to sample the apparatus at an interval in time.

18. The apparatus of claim 17 wherein said timing circuit is operable to reset said detection means at an interval in time.

19. A method for detecting the presence of a chemical, biological or physical component in a monitored area, said method comprising:

providing a capacitive transducer having at least one cantilever spring element secured thereto, said cantilever element having an area thereof coated with a chemical having an affinity for said component to be detected;

providing a pick-up plate positioned adjacent to said cantilever element at a distance such that a capacitance between said cantilever element and said pick-up plate changes as said distance between said cantilever element and said pick-up plate varies, said change in capacitance being a measurable variation;

providing a means for detecting said measurable variation, said measurable variation providing a first signal indicating a change in capacitance that forms a measurement channel signal, said change in capacitance due to the absorption of said component by said coated area of said cantilever element;

providing at least one feedback cantilever spring element for producing a reference channel signal, said reference channel signal providing a second signal; and comparing said first signal to said second signal to produce a resultant signal achieving a common mode cancellation between the measurement channel signal and reference channel signal, said resultant signal related to an accumulation of said component on said coated area of said at least one cantilever.

20. The method of detecting according to claim 19 wherein said steps of providing a first signal and a second signal comprise providing first and second analog signals.

21. The method of detecting according to claim 19 wherein said step of comparing further comprises subtracting said first analog signal from said second analog signal to produce said resultant signal, said resultant signal further converted to a digital signal.

22. The method of detecting according to claim 21 wherein said first and second analog signals are converted to digital signals before said step of subtracting.

* * * * *